United States Patent [19]

Obersat et al.

[11] Patent Number: 5,040,985

[45] Date of Patent: Aug. 20, 1991

[54] ATTACHMENT FOR RELEASABLY COUPLING COMPONENTS OF DENTAL PROSTHESES

[76] Inventors: Adam Obersat, Logenstrasse 4, D-6750 Kaiserslautern; Franz J. Klein, Am Marktplatz 9, D-8944 Grönenbach; Claus-Peter Fritzen, An der Sommerhalde 50, Kaiserslautern, all of Fed. Rep. of Germany

[21] Appl. No.: 547,756

[22] Filed: Jul. 2, 1990

[30] Foreign Application Priority Data

Jun. 30, 1989 [DE] Fed. Rep. of Germany ... 8907997[U]
Jun. 30, 1989 [DE] Fed. Rep. of Germany ... 8908002[U]

[51] Int. Cl.$^5$ ............................................. A61C 13/271
[52] U.S. Cl. ..................................... 433/181; 433/177
[58] Field of Search ............... 433/177, 178, 180, 181, 433/182

[56] References Cited

U.S. PATENT DOCUMENTS

| | | |
|---|---|---|
| 1,688,145 | 10/1928 | Jurgensen ........................... 433/182 |
| 1,743,871 | 1/1930 | Stern ................................... 433/177 |
| 2,803,060 | 8/1957 | Weiss .................................. 433/177 |
| 3,047,952 | 8/1962 | Yamamoto .......................... 433/178 |
| 3,089,242 | 5/1963 | Weissman ........................... 433/177 |
| 4,362,509 | 12/1982 | Sulc .................................... 433/181 |
| 4,579,528 | 4/1986 | Staubli ................................ 433/181 |
| 4,586,902 | 5/1986 | Obersat .............................. 433/177 |
| 4,715,817 | 12/1987 | Zuest et al. ........................ 433/177 |
| 4,773,859 | 9/1988 | Obersat .............................. 433/177 |

FOREIGN PATENT DOCUMENTS 0263235 4/1987 European Pat. Off. .
0136671 1/1988 European Pat. Off. .

*Primary Examiner*—John J. Wilson
*Assistant Examiner*—Jeffrey A. Smith
*Attorney, Agent, or Firm*—Peter K. Kontler

[57] ABSTRACT

An attachment which secures the removable component of a dental prosthesis to the stationary component has complementary male and female detent members one of which is mounted in or on the stationary component and the other of which is mounted on or in the removable component. The detent member on the removable component is separably locked to the detent member on the stationary component in a predetermined position by a locking device having a socket in one of the detent members and a coupling member on the other detent member. The coupling member has a hollow rotary cylindrical, spherical or barrel-shaped rolling element which is mounted on a piece of wire having end portions anchored in the other detent member, separably secured to the other detent member or received in a flat housing on the other detent member. The rolling element can penetrate into and is biased against the surface surrounding the socket. The end portions of the wire can constitute torsion springs or can be installed in a mass of elastomeric material. A cushion can be provided to bias the rolling element into the socket when the movalbe detent member reaches the predetermined position relative to the detent member on the stationary component of the prosthesis. The coupling member can be mounted on the movable detent member to facilitate cleaning by a jet of hydraulic or pneumatic fluid.

23 Claims, 3 Drawing Sheets

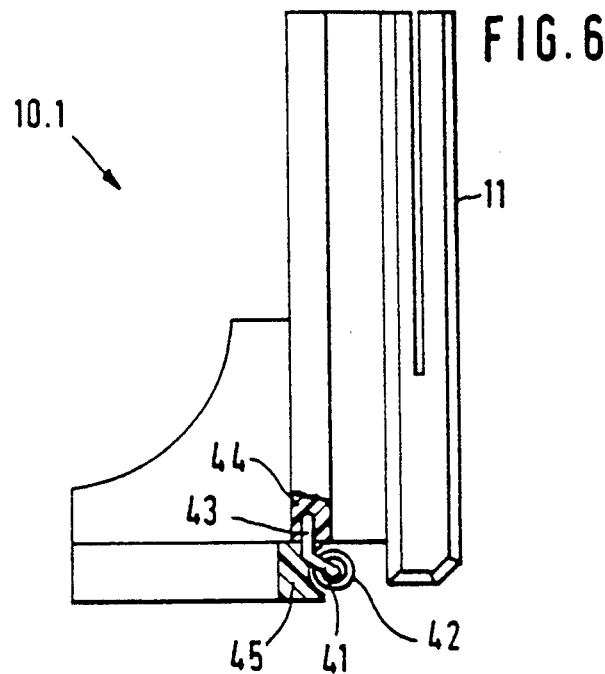
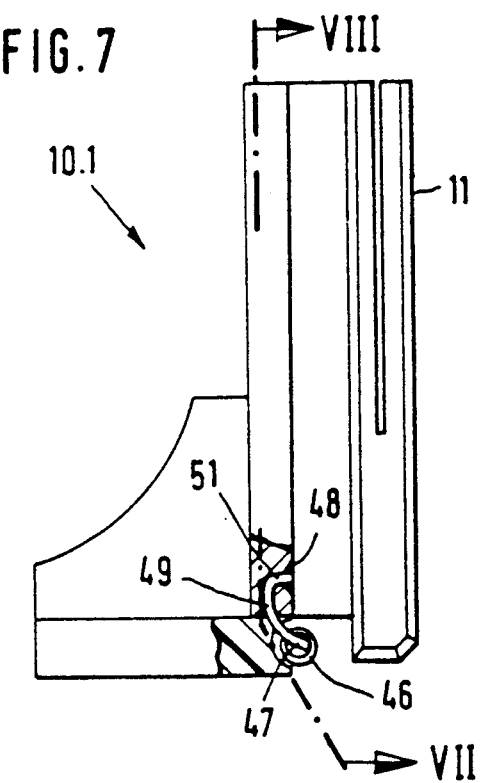
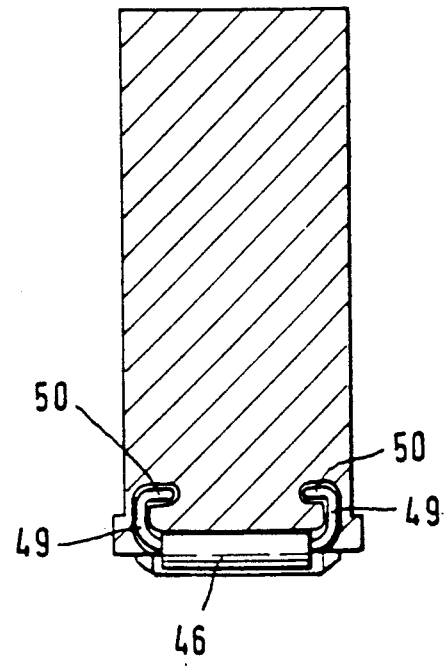

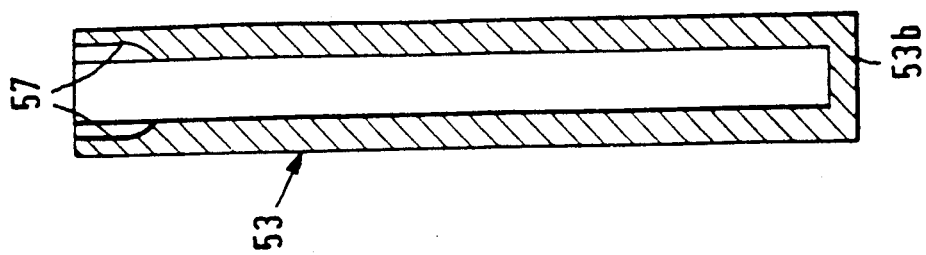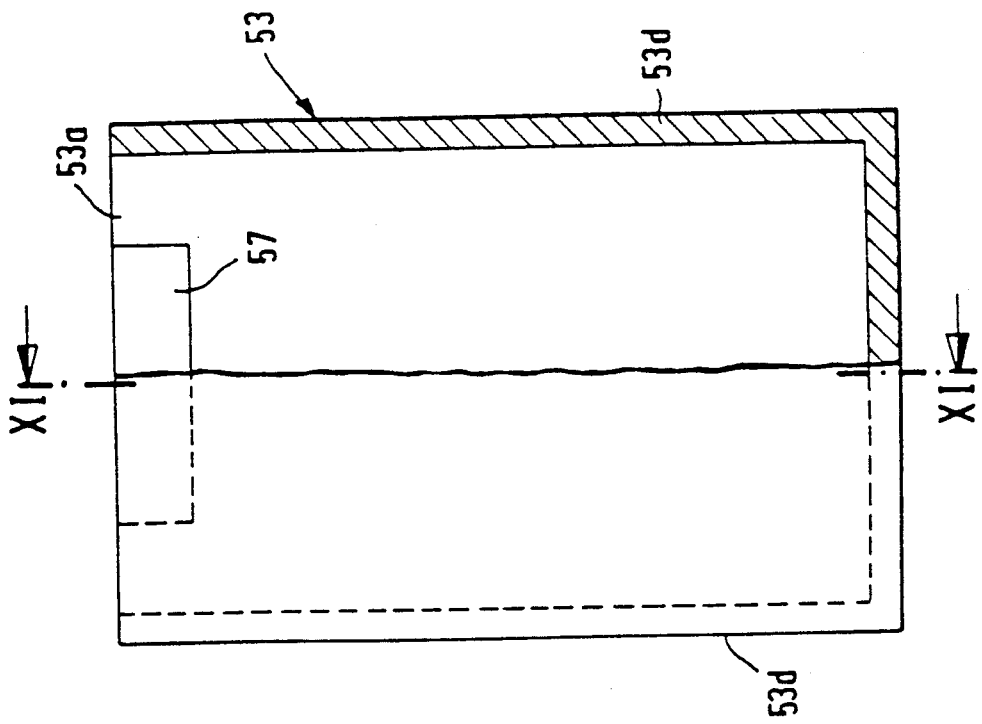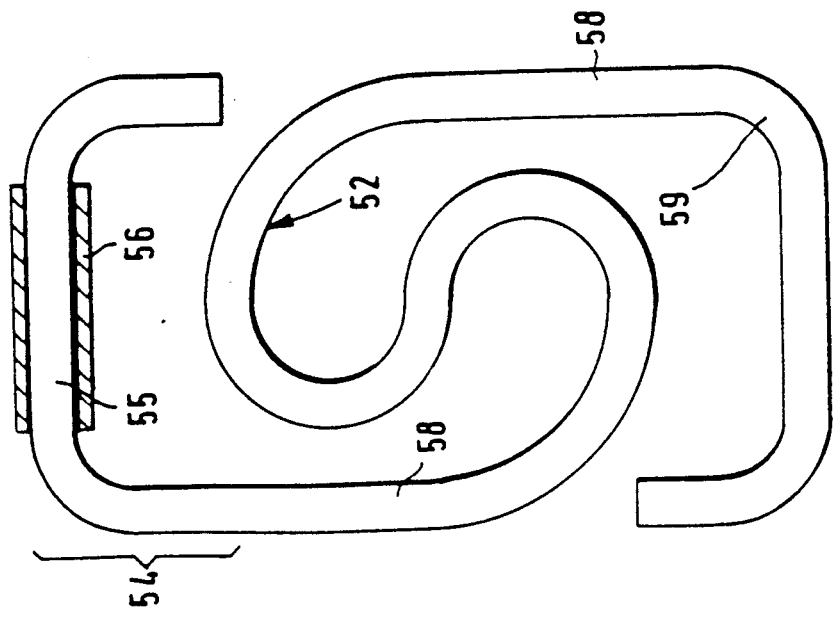

ATTACHMENT FOR RELEASABLY COUPLING COMPONENTS OF DENTAL PROSTHESES

CROSS-REFERENCE TO RELATED CASES

The attachment of the present invention constitutes an improvement over and a further development of attachments which are disclosed in commonly owned U.S. Pat. Nos. 4,586,902 and 4,773,859. The disclosures of these patents are incorporated herein by reference.

BACKGROUND OF THE INVENTION

The invention relates to dental prostheses in general, and more particularly to improvements in attachments which serve to connect stationary and removable components of dental prostheses. Still more particularly, the invention relates to improvements in devices which are used to releasably lock male and female detent members of attachments serving to connect removable and stationary components of dental prostheses to each other.

Commonly owned published European patent applications Nos. 136 671 and 263 235 and the aforementioned commonly owned U.S. Pat. Nos. 4,586,902 and 4,773,859 disclose attachments which employ complementary male and female detent members one of which is mounted in or on the stationary component and the other of which is mounted on or in the removable component of a dental prosthesis. The attachment further comprises a device which serves to releasably lock the detent member for the removable component to the detent member for the stationary component when the two detent members assume predetermined positions relative to each other, i.e., when the removable component is in an optimum position relative to the stationary component of the dental prosthesis. For example, the female detent member can be provided with one or more grooves to slidably receive one or more complementary parts of the male detent member, and the detent member which is provided on the removable component can be locked to the other detent member by a spring which is confined in a flat housing and a portion of which can snap into a complementary recess. The recess is provided in one of the detent members and the housing for the spring is provided on or in the other detent member. The spring can resemble the letter S or the numeral five and can be made of resilient metallic wire. Problems can arise when the spring and/or its housing must be cleaned to remove confined saliva and/or fragments of food and/or other foreign matter which is likely to undergo fermentation and can generate undesirable odors. Moreover, the spring and its housing are very small so that they cannot be readily manipulated by the wearer of the dental prosthesis. This means that the wearer must visit a dentist at frequent intervals for the sole purpose of having the detent members and the locking device for the movable detent member inspected and/or cleaned.

The published European patent application No. 263 235 discloses the possibility of replacing the aforementioned S-shaped or like wire spring with a block of silicone rubber which completely or nearly completely fills the flat housing of the locking device and carries a wear-resistant metallic element capable of entering a complementary recess in order to lock the movable detent member to the other detent member. The block prevents or reduces the likelihood of penetration of saliva, fragments of food and/or other foreign matter into the housing. However, the useful life of a locking device which employs a block of silicone rubber or a like material is relatively short and, moreover, a rubber block is less appetizing in the mouth than a spring of steel wire or the like. The published European patent application No. 263 235 further proposes to use a wear-resistant element in the form of a solid cylinder with two coaxial stubs which are rotatably mounted in the block of silicone rubber or the like. It has been found that proper mounting of stubs in the elastic block presents many problems and, therefore, such locking device was never actually made and/or used.

OBJECTS OF THE INVENTION

An object of the invention is to provide novel and improved attachment which can separably connect complementary male and female detent members for stationary and removable components of dental prostheses.

Another object of the invention is to provide the attachment with a novel and improved device which can releasably lock the male and female detent members in a single predetermined position or in one of two or more different predetermined positions relative to each other.

A further object of the invention is to provide a locking device which generates a minimum of friction during coupling of detent members to or during separation of detent members from each other.

An additional object of the invention is to provide a locking device which is less likely to retain saliva, fragments of food and/or other foreign matter than heretofore known locking devices.

Still another object of the invention is to provide a locking device which comprises a minimal number of simple parts and which can be readily withdrawn from a wearer's mouth to facilitate inspection, repair and/or cleaning of its parts.

A further object of the invention is to provide a locking device which can be inspected, cleaned and reinserted by the wearer of the dental prosthesis.

An additional object of the invention is to provide detent members which are combined with or embody a locking device of the above outlined character.

Another object of the invention is to provide a simple, compact and inexpensive locking device which can be installed on or otherwise combined with existing detent members for attachment of removable components of dental prostheses to or their detachment from stationary components.

An additional object of the invention is to provide a reliable locking device which can be used as a superior substitute for heretofore known locking devices.

SUMMARY OF THE INVENTION

The invention resides in the provision of a separable attachment between stationary and removable components of a dental prosthesis. The improved attachment comprises a female detent member on one of the components, and a male detent member provided on the other of the components and separably engaging the female detent member. The detent member on the removable component is movable relative to the detent member on the stationary component to and from at least one predetermined position, and the attachment further comprises means for releasably locking the movable detent member in the at least one predetermined position. The locking means includes a socket in one of the detent members and a coupling member in the other detent member. The coupling member comprises a hollow rolling element which extends into the socket in the at least one predetermined position of the movable detent member, and a shaft which is secured to the other detent member and extends into the hollow rolling element. The attachment preferably further comprises means for yieldably biasing the rolling element into the socket in the at least one predetermined position of the movable detent member, and the shaft forms part or can form part of such biasing means.

The coupling means can comprise a length of wire which is secured to the other detent member, and a portion of the wire can constitute the shaft for the rolling element. The latter can constitute a cylinder, a barrel or a portion of a sphere (even an entire sphere). The wire is or can be resilient and preferably comprises two end portions which flank the shaft and are secured to the other detent member. For example, the end portions can be anchored in (such as bonded to by welding, soldering or by means of an adhesive) the other detent member. The other detent member can be provided with pockets (e.g., in the form of blind holes or bores), and the end portions of the wire can be withdrawably inserted into the pockets, i.e., the end portions of the wire can be repeatedly inserted into and withdrawn from the pockets to permit replacement of the wire and/or rolling element or an inspection or cleaning of such parts.

The other detent member can comprise an elastomeric portion, and the end portions of the wire can be anchored in the elastomeric portion of the other detent member. The elastomeric portion can constitute a separately produced part of the other detent member. If desired, the end portions of the wire can be provided with barbs or hooks to facilitate the establishment of reliable connections between the end portions and the other detent member and/or to reinforce the connection between the end portions and the other detent member.

The shaft can have an arcuate shape and is stressed and thereby flattened when the rolling element extends into the socket. The inner diameter of the hollow rolling element can exceed the diameter of the shaft. Furthermore, the end portions of the wire can be inclined relative to the shaft and can store energy when the rolling element extends into the socket to thus reduce the likelihood of unintentional expulsion of the rolling element from the socket. Each end portion is or can be (at least in part) normal to the axis of rotation of the rolling element relative to the shaft. It is also possible to select the configuration of the wire in such a way that its end portions make oblique angles with the axis of rotation of the rolling element relative to the shaft. At least one end portion of the wire can constitute a torsion spring which is deformed and stores energy during introduction of the rolling element into the socket and/or when the rolling element is received in the socket. If each end portion of the wire constitutes or includes a torsion spring, such torsion springs are or can be substantially coaxial with each other.

The movable detent member is or can be slidable relative to the detent member on the stationary component in order to move to or from the at least one predetermined position. Each detent member can constitute a prefabricated part which is affixed to the respective component of the dental prosthesis. The coupling member can be provided on the movable detent member so that it can be readily inspected, cleaned or replaced subsequent to separation of the movable detent member from the detent member on the stationary component of the prosthesis. This coupling member is or can be installed on the movable detent member in such position that it is adjacent the gum of the wearer of the prosthesis when the movable detent member is connected with the detent member on the stationary component and the rolling element extends into the socket.

It is also possible to employ a coupling member having a length of resilient wire a first portion of which constitutes the shaft for the rolling element and which further comprises a bent second portion confined in a flat housing of the coupling member. The wire can have a substantially square or rectangular outline, and the first portion (shaft) of such wire is or can be substantially straight. The second portion of the wire can include two spaced apart sections which are substantially normal to the shaft. A section of the second portion of the wire is spaced apart from and can be at least similar to the first portion which includes the shaft. The housing can be provided with an opening for the first portion of the wire and can include an end wall opposite the opening. The second portion of the wire has a section which reacts against the end wall of the housing when the rolling element is received in the socket to thereby bias the rolling element against the one detent member.

The novel features which are considered as characteristic of the invention are set forth in particular in the appended claims. The improved attachment itself, however, both as to its construction and its mode of operation, together with additional features and advantages thereof, will be best understood upon perusal of the following detailed description of certain presently preferred specific embodiments with reference to the accompanying drawing.

BRIEF DESCRIPTION OF THE DRAWING

FIG. 6 shows a male detent member which is similar to that of FIG. 1 and a fourth coupling member;

FIG. 7 is a view similar to that of FIG. 6 but showing a fifth coupling member constituting a modification of the coupling member of FIG. 6;

FIG. 8 is a sectional view substantially as seen in the direction of arrows from the line VIII—VIII of FIG. 7;

FIG. 9 is a greatly enlarged plan view of the wire and rolling element forming part of a further coupling member;

FIG. 10 is a partly elevational and partly sectional view of a housing for the wire of FIG. 9; and FIG. 11 is a sectional view substantially as seen in the direction of arrows from the line XI—XI of FIG. 10.

DESCRIPTION OF PREFERRED EMBODIMENTS

Figure 1:
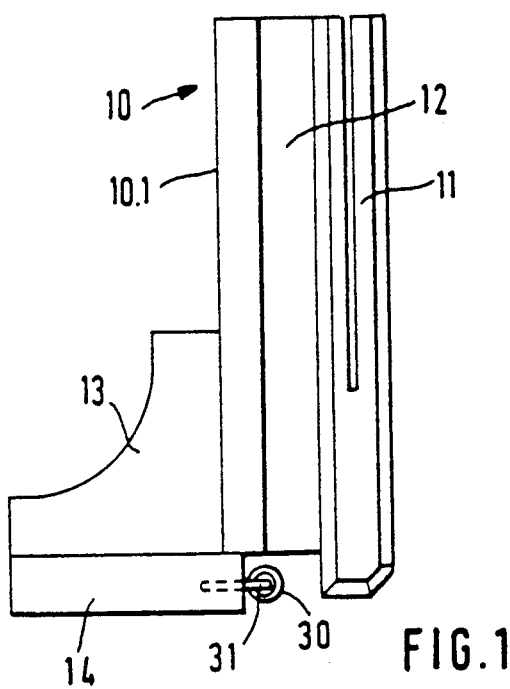
FIG. 1 is an enlarged schematic elevational view of a male detent member which carries the coupling member of a locking device embodying one form of the present invention.
Figure 2:
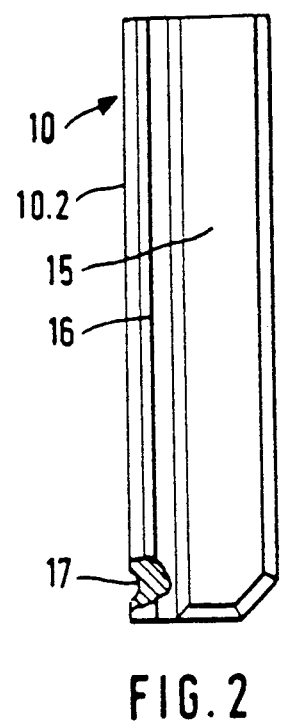
FIG. 2 is a similar enlarged schematic partly elevational and partly sectional view of a complementary female detent member which is provided with a socket for the rolling element of coupling member on the male detent member of FIG. 1.
Figure 3:
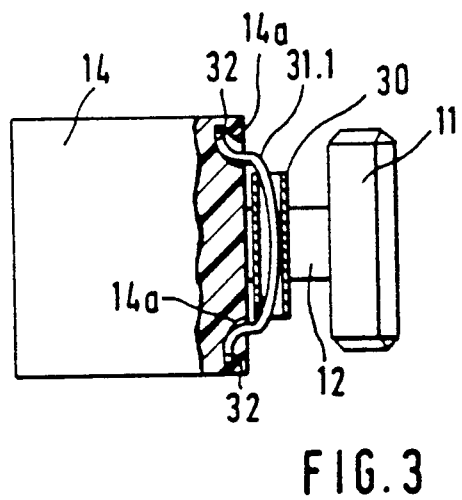
FIG. 3 is a bottom plan view of the male detent member which is partly broken away to expose the wire of the male coupling member.
Figure 4:
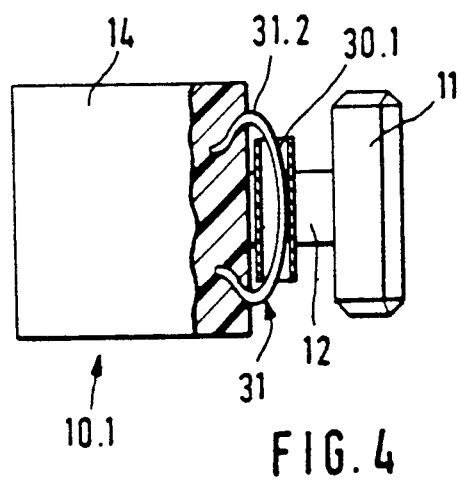
FIG. 4 is a bottom plan view corresponding to that of FIG. 3 but showing a modified coupling member.

FIGS. 1 to 3 illustrate a first embodiment of an attachment 10 which embodies the present invention. The attachment 10 comprises a male detent member 10.1 which is provided on one component of a dental prosthesis (not shown), for example, on a removable component (bridge) of the type shown in FIG. 4 of commonly owned U.S. Pat. No. 4,773,859. A female detent member 10.2 of the attachment 10 is connected to or forms part of a stationary component of the prosthesis, such as the crown which is shown in FIG. 4 of U.S. Pat. No. 4,773,859.

The male detent member 10.1 comprises a slotted spring 11 the rear side of which is adjacent a narrower neck portion 12. The spring 11 is slidable in a groove 15 of the female detent member 10.2 to and from a predetermined position in which a coupling member 30, 31 on the detent member 10.1 extends into a socket 17 of the detent member 10.2. The socket 17 and the coupling member 30, 31 together constitute a locking device which can releasably retain the detent member 10.1 in the predetermined position relative to the detent member 10.2. If the detent member 10.2 has two or more sockets 17, the male detent member 10.1 can be releasably locked in two or more different predetermined positions relative to the detent member 10.2.

The detent members 10.1 and 10.2 can constitute commercially available parts of a so-called friction grip slide attachment, and a feature of the present invention resides in the provision of a novel coupling member which can cooperate with the single socket 17 or with any one of two or more sockets to releasably lock the movable male detent member 10.1 in a single predetermined position (or in one of two or more predetermined positions) relative to the female detent member 10.2. The latter has a slot-shaped opening 16 which is adjacent the groove 15 for the spring 11 and serves to receive the neck portion 12 of the male detent member 10.1. The spring 11 stores energy when it extends into the groove 15 of the female detent member 10.2 to thus ensure that the removable component of the dental prosthesis cannot wobble relative to the stationary components when such components are separably connected to each other by the attachment including the detent members 10.1 and 10.2.

The coupling member 30, 31 is mounted on a module 14 which is or can constitute a separately produced part and is affixed to the main portion of the male detent member 10.1 by a reinforcing rib 13 or a like part. The module 14 has a front side facing the adjacent portion of the spring 11 and supporting the coupling member of the locking device. The coupling member includes a rolling element in the form of a relatively short hollow cylinder 30, and a length of resilient wire 31 having a centrally located portion 31.1 constituting a shaft for the rolling element 30 and two end portions 32 which flank the shaft 31.1 and are separably secured to the module 14 of the male detent member 10.1. The shaft 31.1 has an arcuate shape and its diameter is less than the inner diameter of the hollow cylindrical rolling element 30. The latter is caused to snap into the socket 17 when the male detent member 10.1 reaches the predetermined position relative to the female detent member 10.2, and the wire 31 thereupon prevents accidental expulsion or extraction of the rolling element 30 from the socket 17. An advantage of the rolling element 30 and of its mounting on the median portion or shaft 31.1 of the resilient wire 31 is that friction between the rolling element and the female detent member 10.2 during sliding movement of the detent member 10.1 toward or away from its predetermined position is minimal. Thus, the magnitude of the locking force with which the detent member 10.1 is held in the predetermined position depends exclusively upon the dimensions of the socket 17 and rolling element 30 as well as upon the bias of the wire 31 including the shaft 31.1.

As can be seen in FIG. 3, the mounting of the end portions 32 of the wire 31 in the pockets 14a (such pockets can constitute blind holes or blind bores) of the module 14 is such that the rolling element 30 can move in a number of directions including toward and away from the adjacent front face of the module 14 as well as in substantial parallelism with such front face, i.e., longitudinally of the spring 11. Such practically universal movability of the rolling element 30 relative to the module 14 can be achieved even if the wire 31 is relatively short. The shaft 31.1 is or can be at least slightly flattened when a portion of the rolling element 30 extends into the socket 17, i.e., the wire 31 then biases the peripheral surface of the rolling element 30 against the surface bounding the socket 17. The end portions 32 of the wire 31 are repeatedly insertable into and withdrawable from the respective pockets 14a; this renders it possible to repeatedly inspect the wire and the rolling element 30 and to rinse or wash the coupling member 30, 31 with a jet of water or compressed air. Any fragments of food which gather in the axial passage of the cylindrical rolling element 30 are loosened by turning the rolling element on its shaft 31.1 to thus further facilitate expulsion of contaminants from the interior of the rolling element by pneumatic and/or hydraulic means. The form-locking connection which is established when the end portions 32 of the wire 31 are properly received in the respective pockets 14a is sufficiently reliable to ensure that the movable male detent member 10.1 does not leave its predetermined position relative to the stationary female detent member 10.2 until and unless the rolling element 30 is intentionally expelled from the socket 17 by a dental technician, by a dentist or by the wearer of the prosthesis including the components which are separably secured to each other by the improved attachment 10.

The wire 31 can be rigid and can be biased toward the spring 11 by one or more springs, e.g., coil springs. Furthermore, the wire 31 can be replaced by a coil spring one end portion of which extends into and constitutes a shaft for the rolling element 30.

FIG. 4 shows that the rolling element 30.1 of the coupling member can resemble or constitute a hollow barrel and that the end portions 31.2 of the wire 31 can be provided with outwardly extending barbs or hooks in order to enhance the reliability of connection between the wire and the module 14 of the male detent member 10.1. The end portions 31.2 of the wire 31 are anchored in (e.g., simply embedded into the material of) the module 14. Thus, the wire 31 can be more or less permanently secured to the module 14. This does not appreciably affect the facility with which the barrel-shaped rolling element 30.1 can be cleaned by a jet of water or a stream of compressed air because the module 14 preferably forms part of the movable detent member 10.1 which latter can be detached from the detent member (10.2) on the stationary component of the prosthesis. This enables a patient, a dental technician or a dentist to remove the module 14 and the coupling member 30.1, 31 from the mouth of the wearer of the prosthesis for convenient inspection, cleaning and/or repair. It is also possible to permanently embed or anchor the end portions 31.2 of the wire in the material of the module 14 by welding or by resorting to a suitable adhesive. The wire 31 of FIG. 4 can carry a hollow cylindrical rolling element 30 or a hollow rolling element (not specifically shown) which forms part of or constitutes a sphere.

The module 14 can be made of an elastomeric material. This contributes to movability of the rolling element 30 or 30.1 relative to the spring 11 of the male detent member 10.1 during movement of the male detent member toward or from its predetermined position relative to the female detent member 10.2. An elastic module 14 exhibits the additional advantage that it reduces the likelihood of breakage of the wire 31, especially in the regions where the end portions 32 or 31.2 of the wire extend into the material of the module.

Figure 5:
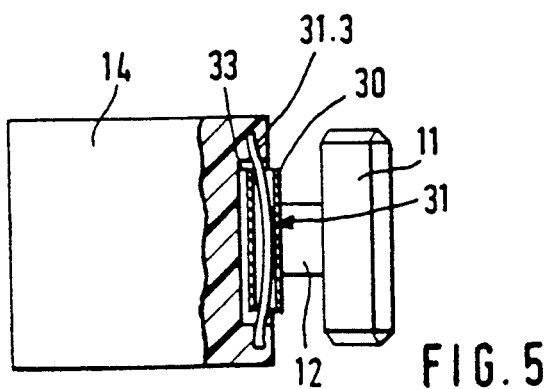
FIG. 5 is a bottom plan view corresponding to that of FIG. 3 but showing a third coupling member.

FIG. 5 shows that the front face of the module 14 can be provided with a recess 33 for a portion of the hollow cylindrical rolling element 30. This reduces the likelihood of injury to the wearer or the prosthesis during attachment of the male detent member (including the module 14) to or during its separation from the other detent member. Moreover, the partly recessed rolling element 30 of FIG. 5 is less likely to be damaged during cleaning of the male detent member which includes the module 14 of FIG. 5. The end portions 31.3 of the wire 31 which is shown in FIG. 5 are anchored in the material of the module 14. However, it is equally possible to provide the module 14 of FIG. 5 with pockets (such as the pockets 14a of FIG. 3) which removably receive the end portions of the wire. Furthermore, the end portions of the wire for the rolling element 30 of FIG. 5 can be provided with barbs to enhance the retaining action between such barbed end portions and the module 14.

The improved coupling member including a rolling element and a wire can be used with equal advantage on other types of detent members, e.g., on a movable detent member which does not employ a module 14. Furthermore, the detent member which carries the rolling element and the wire need not be slidable relative to the other detent member; for example, the rolling element and its wire can be mounted directly on a detent member in the form of a bridge which is separably connectable to a detent member in the mouth of the wearer of a dental prosthesis. All that counts is to provide one of two cooperating separable detent members with one or more sockets and to provide the other of these detent members with a coupling member including at least one hollow rolling element on a shaft which can constitute a portion of a length of wire and can enter the single socket or a selected socket of the one detent member in order to releasably lock the other detent member to the one detent member.

The male detent member 10.1 of FIG. 6 is identical with the similarly referenced detent member of FIG. 1. The coupling member of FIG. 6 comprises a hollow cylindrical rolling element 42 and a resilient wire 41 having a shaft which extends through the axial passage of the rolling element 42. The end portions 43 of the wire 41 are bent twice at right angles to the axis of the rolling element 42, once in the direction of penetration of the rolling element into the socket 17 (not shown in FIG. 6) and once in parallelism with the longitudinal direction of the spring 11. The tips of the end portions 43 are bent to extend in parallelism with the axis of the rolling element 42 and are anchored in the adjacent portion 44 of the male detent member 10.1. The inner diameter of the rolling element 42 need not appreciably exceed the diameter of that (median) portion of the wire 41 which constitutes the shaft, especially if the shaft is straight. If the shaft of the wire 41 is substantially straight, i.e., if the inner diameter of the rolling element 42 need not appreciably exceed the diameter of the shaft, the outer diameter of the rolling element 42 can be reduced accordingly. This is often desirable and advantageous because it entails a reduction of the overall dimensions of the exposed part of the coupling member including the rolling element 42 and the wire 41. The portion 44 of the detent member 10.1 can constitute a mass of hardened plastic or other suitable material (e.g., solder) which confines the tips of end portions 43 of the wire 41. It is also possible to use a mass of elastomeric plastic material; the tip of each end portion 43 then preferably resembles the letter L or V to ensure more reliable anchoring of such tips in the elastic mass which constitutes the portion 44.

FIG. 6 further shows an elastic cushion 45 which is located behind the hollow rolling element 42 and has a concave recess with a radius of curvature matching or approximating the radius of the peripheral surface of the rolling element. When the male detent member 10.1 of FIG. 6 engages a complementary female detent member (such as the detent member 10.2 of FIG. 2), the wire 41 is stressed to store energy and cooperate with the elastic cushion 45 to bias the rolling element 42 into the socket of the complementary detent member with a predetermined force. The female detent member can be provided with a cam face (not specifically shown in FIG. 2) which gradually presses the rolling element 42 toward and into the recess of the cushion 45 and causes the wire 41 to store energy during introduction of the spring 11 into the groove 15 of the female detent member.

It will be noted that the rolling element 42 of FIG. 6 can be biased into the socket of the female detent member in several ways, namely by the elastic mass of the portion 44, by the stressed wire 41 and by the elastic cushion 45. The latter serves as a back support which further reduces the likelihood of accidental expulsion of the rolling element 42 from the socket of the female detent member.

FIGS. 7 and 8 show a male detent member 10.1 which carries a modified coupling member including a hollow cylindrical rolling element 46 and a resilient metallic or plastic wire 47 having two mirror symmetrical end portions 49 extending into a portion 48 of the male detent member behind the spring 11. The tips 50 of end portions 49 extend at right angles to the axis of the rolling element 46 and are welded or soldered to the portion 48. The free end portions 51 of the tips 50 are bent toward the spring 11 at right angles to the axis of the rolling element 46. The major parts of the end portions 49 are arcuate (see FIG. 7). Each of these end portions can be said to include or constitute a torsion spring which enables the rolling element 46 to move forwardly toward and rearwardly away from adjacent portion of the spring 11. That (median) portion of the wire 47 which constitutes a shaft for the rolling element 46 is straight or has a slightly arcuate shape. The same holds true for the median portion of the wire 41 which is shown in FIG. 6.

FIGS. 9 to 11 show a further coupling member which remotely resembles that shown in FIG. 1 of U.S. Pat.

No. 4,586,902 or 4,773,859. The front portion or section 54 of the resilient wire 52 is a U-shaped body having a substantially straight web 55 constituting a shaft for a hollow cylindrical rolling element 56. The latter normally extends outwardly beyond the opening 53a in a flat rectangular or square housing 53 for the wire 52. The rear portion or section 59 of the wire 52 reacts against the end wall 53b of the housing 53 when the wire is properly received in the housing 53, and the wire stores energy when the rolling element 56 rolls along the female detent member (not shown in FIGS. 9 to 11) on its way into a single socket or into one of two or more sockets. The wire 52 is disposed in a plane so that it can fit into the narrow chamber 53c of the housing 53. The opening 53a is bounded by two recesses 57 which serve to receive the adjacent portions of the rolling element 56 when the latter is depressed into the housing 53 during movement of the male detent member relative to the female detent member in a direction to move the rolling element toward or away from the socket.

The wire 52 has a square or rectangular outline to be a snug fit in the chamber 53c of the housing 53. This wire has two spaced-apart substantially parallel sections or portions 58 which are normal to the shaft 55. The portions or sections 58 are adjacent the respective narrow sidewalls 53d of the housing 53 when the major part of the wire 52 is received in the chamber 53c.

That portion of the chamber 53c which is not occupied by the wire 52 can be filled with an elastomeric material, not shown. This reduces the likelihood of penetration of saliva and/or fragments of food into the chamber 53c. The median portion of the wire 52 is S-shaped; however this median portion can also resemble the letter U or can have a more complex configuration, for example, in order to substantially fill the chamber 53c especially when the rolling element 56 is depressed into the recesses 57 at the opening 53a of the housing 53. An advantage of the wire 52 is that it has a soft spring characteristic and that its bias upon the rolling element 56 can be selected with a high degree of accuracy.

The wire 52 constitutes an improvement over the wires which are disclosed in the aforementioned commonly owned U.S. Pats. Nos. 4,586,902 and 4,773,859. This wire can be used as a coupling member with or without the rolling element 56.

An advantage of the improved locking device is that the hollow cylindrical, barrel-shaped or spherical rolling element can be mounted on a length of wire in a simple, inexpensive and reliable manner. The rolling element can simply roll along the female detent member 10.2 (if the wire is mounted in or on the male detent member 10.1) on its way toward or away from the socket 17 or on its way toward or away from one of two or more sockets. It is no longer necessary to employ a solid cylinder with stubs which are to be rotatably received in a mass of elastomeric material. The hollow rolling element reduces frictional sliding engagement between the two detent members during travel of the rolling element toward or away from a socket so that the detent members are subject to less pronounced wear. Thus, if and when necessary, a dentist can replace a spent rolling element but the major part of the attachment including such rolling element remains intact or has undergone much less wear than in the absence of a rolling element.

As shown in the drawing and as already explained above, it is advisable to mount the coupling member (including the rolling element) on the movable detent member, i.e., on the detent member which is secured to or forms part of the separable component of a dental prosthesis. This ensures that the coupling member including the rolling element and the wire is automatically withdrawn from the mouth when the removable component of the prosthesis is withdrawn so that the coupling member is exposed for inspection, cleaning or replacement. The attachment is preferably designed or can be designed in such a way that the wear upon the detent member on the removable component of the prosthesis is more pronounced than the wear upon the other detent member which is affixed to or forms part of the stationary component. The reason is that it is much simpler and less expensive to replace or repair the detent member on the removable component of the prosthesis.

The rolling element of the improved coupling member not only reduces friction during movement of the movable detent member relative to the other detent member, but such rolling element also facilitates cleaning of the coupling member. Thus, any foreign matter which is confined in and adheres to the surface surrounding the axial passage of the rolling element is loosened by rotating the rolling element on its shaft preparatory to flushing out the thus loosened foreign matter with a jet of water, another liquid, compressed air or another gaseous fluid.

Another advantage of a coupling member which employs a rolling element is that such coupling member can engage the surface around a socket with a force of predictable magnitude and orientation. This enables the dentist to select that force which is best suited to prevent accidental separation of the movable detent member from the other detent member but is not so large as to offer excessive resistance to intentional separation of the movable detent member from the other detent member.

It is presently preferred to employ rolling elements in the form of hollow cylinders. Such rolling elements can be mass-produced at a reasonable cost, e.g., by severing an available piece of hollow metallic or other suitable tubular stock.

The wire which includes a shaft for the rolling element need not be made of a resilient material. For example, the wire 41 of FIG. 6 or the wire 47 of FIGS. 7-8 can be made of rigid metallic material. However, the utilization of a resilient wire exhibits numerous advantages. Thus, it is not necessary to provide additional parts (such as the mass 44 shown in FIG. 6) to ensure that the rolling element can yield in one or more directions during movement of the detent member 10.1 relative to the detent member 10.2. As already described above, the configuration of a resilient wire can be such that the respective rolling element has freedom of movement in two or more different directions to thus even further reduce friction and to be capable of yielding during movement toward or away from a single socket 17 or a selected socket.

Another advantage of a coupling member which employs a length of wire as a shaft for the rolling element and as a means for removably or more or less permanently securing the rolling element to the respective detent member is that the space requirements of a piece of suitably bent or shaped wire are negligible.

It is often advisable to complete the making of the detent members prior to connection of one of the detent members with a coupling member. This simplifies the making of the detent members. The socket 17 is thereupon machined into or is otherwise formed in one of the finished detent members, and a prefabricated coupling member is affixed to the other detent member. Separately produced coupling members can be separably or permanently affixed to existing male or female detent members. Moreover, such coupling members can be affixed to the male or female detent members of mass-produced attachments which are used to separably secure removable components of dental prostheses to stationary components.

The utilization of a wire which includes one or more torsion springs, barbs and specially bent and inclined portions or sections further enhances the yieldability of the rolling element in one, two or more directions to thus reduce friction and wear and to prolong the useful life of the locking device for the male and female detent members as well as the useful life of the entire attachment.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. A separable attachment between stationary and removable components of a dental prosthesis, comprising a female detent member on one of the components; a male detent member provided on the other of the components and separably engaging said female detent member, the detent member on the removable component being movable relative to the detent member on the stationary component to and from at least one predetermined position; means for releasably locking said movable detent member in said at least one predetermined position, including a socket in one of said detent members and a coupling member on the other of said detent members, said coupling member comprising a hollow rolling element which extends into said socket in said at least one predetermined position of said movable detent member and a shaft secured to said other detent member and extending into said rolling element; and means for yieldably biasing said rolling element into said socket in said at least one predetermined position of said movable detent member, said shaft forming part of said biasing means.

2. The attachment of claim 1, wherein said movable detent member is slidable relative to the detent member on the stationary component to and from said at least one predetermined position, each of said detent members constituting a prefabricated part affixed to the respective component.

3. The attachment of claim 1, wherein said movable detent member is slidable relative to the detent member on the stationary component to and from said at least one predetermined position, said coupling member being provided on said movable detent member and being adjacent the gum of the wearer of the prosthesis in said one predetermined position of said movable detent member.

4. A separable attachment between stationary and removable components of a dental prosthesis, comprising a female detent member on one of the components; a male detent member provided on the other of the components and separably engaging said female detent member, the detent member on the removable component being movable relative to the detent member on the stationary component to and from at least one predetermined position; and means for releasably locking said movable detent member in said at least one predetermined position, including a socket in one of said detent members and a coupling member on the other of said detent members, said coupling member comprising a hollow rolling element which extends into said socket in said at least one predetermined position of said movable detent member and a shaft secured to said other detent member and extending into said rolling element, said coupling member further comprising a length of resilient wire including a first portion which constitutes said shaft and a bent second portion, said coupling member also comprising a flat housing for the second of said wire.

5. The attachment of claim 4, wherein said wire has a substantially rectangular or square outline, said first portion being substantially straight and said second portion including two spaced apart sections substantially normal to said first portion.

6. The attachment of claim 4, wherein said second portion includes a section which is spaced apart from and at least similar to said first portion.

7. The attachment of claim 4, wherein said housing has an opening for said first portion and an end wall opposite said opening, said second portion having a section which reacts against said end wall when said rolling element is received in said socket to thereby bias said rolling element against said one detent member.

8. A separable attachment between stationary and removable components of a dental prosthesis, comprising a female detent member on one of the components; a male detent member provided on the other of the components and separably engaging said female detent member, the detent member on the removable component being movable relative to the detent member on the stationary component to and from at least one predetermined position; and means for releasably locking said movable detent member in said at least one predetermined position, including a socket in one of said detent members and a coupling member on the other of said detent members, said coupling member comprising a hollow rolling element which extends into said socket in said at least one predetermined position of said movable detent member and a shaft secured to said other detent member and extending into said rolling element, said coupling member further including a length of wire secured to said other detent member, said wire including a portion which constitutes said shaft.

9. The attachment of claim 8, wherein said wire is resilient and further comprises two end portions flanking said shaft and secured to said other detent member.

10. The attachment of claim 9, wherein said end portions are inclined relative to said shaft and store energy when said element extends into said socket.

11. The attachment of claim 10, wherein said end portions are, at least in part, substantially normal to the axis of rotation of said rolling element relative to said shaft.

12. The attachment of claim 10, wherein said end portions make oblique angles with the axis of rotation of said element relative to said shaft.

13. The attachment of claim 9, wherein said other detent member has pockets for said end portions.

14. The attachment of claim 13, wherein said pockets are holes and said end portions are withdrawable from and reinsertable into the respective holes.

15. The attachment of claim 9, wherein said other detent member comprises an elastomeric portion and said end portions are anchored in said elastomeric portion.

16. The attachment of claim 15, wherein said elastomeric portion is a separately produced part of said other detent member.

17. The attachment of claim 9, wherein at least one of said end portions includes a torsion spring.

18. The attachment of claim 17, wherein each of said end portions includes a torsion spring and said torsion springs are substantially coaxial with each other.

19. The attachment of claim 9, wherein said end portions are barbed.

20. The attachment of claim 9, wherein said shaft has an arcuate shape and is stressed and thereby flattened when said element extends into said socket.

21. The attachment of claim 9, wherein said shaft has an arcuate shape and a first diameter, said rolling element having an inner diameter greater than said first diameter.

22. The attachment of claim 9, wherein said end portions are anchored in said other detent member.

23. The attachment of claim 8, wherein said rolling element is a cylinder.

* * * * *